(12) United States Patent
Heller

(10) Patent No.: US 12,239,419 B2
(45) Date of Patent: Mar. 4, 2025

(54) SYSTEMS FOR REAL TIME FEBRILITY DETECTION AND NOTIFICATION

(71) Applicant: Alan C. Heller, Dallas, TX (US)

(72) Inventor: Alan C. Heller, Dallas, TX (US)

( * ) Notice: Subject to any disclaimer, the term of this patent is extended or adjusted under 35 U.S.C. 154(b) by 661 days.

(21) Appl. No.: 15/604,792

(22) Filed: May 25, 2017

(65) Prior Publication Data

US 2017/0258335 A1 Sep. 14, 2017

Related U.S. Application Data

(60) Continuation of application No. 14/644,057, filed on Mar. 10, 2015, now abandoned, which is a division of application No. 13/668,270, filed on Nov. 3, 2012, now abandoned, and a continuation of application No. PCT/US2014/067780, filed on Nov. 26, 2014.

(60) Provisional application No. 61/609,258, filed on Mar. 9, 2012, provisional application No. 61/628,721, filed on Nov. 4, 2011.

(51) Int. Cl.
  *A61B 5/01* (2006.01)
  *A61B 5/00* (2006.01)

(52) U.S. Cl.
  CPC ............ *A61B 5/015* (2013.01); *A61B 5/0077* (2013.01); *A61B 5/6887* (2013.01)

(58) Field of Classification Search
  CPC .............................. A61B 5/015; A61B 5/0077
  See application file for complete search history.

(56) References Cited

U.S. PATENT DOCUMENTS

| | | | |
|---|---|---|---|
| 5,299,594 A | 4/1994 | Lord | |
| 5,339,687 A | 8/1994 | Gimson | |
| 5,364,132 A * | 11/1994 | Haas | ........................ G04F 1/00 283/67 |
| 5,386,831 A | 2/1995 | Gluck | |
| 5,499,631 A | 3/1996 | Weiland | |
| 5,528,041 A | 6/1996 | Pompei | |
| 5,872,362 A | 2/1999 | Pompei | |
| 5,874,736 A | 2/1999 | Pompei | |
| 5,893,833 A | 4/1999 | Pompei | |

(Continued)

FOREIGN PATENT DOCUMENTS

| | | | |
|---|---|---|---|
| BR | PI0407816 | * | 2/2006 |
| CA | 2229630 | * | 9/1998 |

(Continued)

OTHER PUBLICATIONS

Machine Transation of BR PI0407816, Patent Translate, pp. 1-184, printed on Nov. 28, 2023 (Year: 2006).*

(Continued)

*Primary Examiner* — Daniel L Cerioni
*Assistant Examiner* — Om Patel

(57) ABSTRACT

Systems and processes are presented for real time health credentialing of individuals seeking entry to a facility requiring health credentialing for access. A system and process for real time detection of a febrile condition comprises providing a heat sensor operable to receive thermal radiation from a person. Optionally, the system provides a controller operable to selectively orient the thermal sensor incident to the facial region of a person within a zone of detection. Further, the system optionally processes the sensor temperature to conditionally determine a febrile condition.

14 Claims, 8 Drawing Sheets

(56) References Cited

U.S. PATENT DOCUMENTS

| | | |
|---|---|---|
| 5,894,126 A | 4/1999 | Pompei |
| 6,045,257 A | 4/2000 | Pompei |
| 6,056,435 A | 5/2000 | Pompei |
| 6,100,527 A | 8/2000 | Pompei |
| 6,219,573 B1 | 4/2001 | Pompei |
| 6,241,384 B1 | 6/2001 | Pompei |
| 6,292,685 B1* | 9/2001 | Pompei ............ G01J 5/02 |
| | | 600/475 |
| 6,299,347 B1 | 10/2001 | Pompei |
| 6,402,371 B2 | 6/2002 | Pompei |
| 6,423,970 B1 | 7/2002 | Pompei |
| 6,499,877 B2 | 12/2002 | Pompei |
| 6,547,744 B1 | 4/2003 | Pompei |
| 6,617,581 B2 | 9/2003 | Pompei |
| 6,641,301 B2 | 11/2003 | Pompei |
| 6,677,859 B1 | 1/2004 | Bensen |
| 7,314,309 B2 | 1/2008 | Pompei |
| 7,346,386 B2 | 3/2008 | Pompei |
| 7,787,938 B2 | 8/2010 | Pompei |
| 8,073,535 B2 | 12/2011 | Jung |
| 2004/0114779 A1* | 6/2004 | Blazey ............ G07C 9/20 |
| | | 382/100 |
| 2004/0220538 A1 | 11/2004 | Panopoulos |
| 2007/0153871 A1 | 7/2007 | Fraden |
| 2007/0222554 A1 | 9/2007 | Hart |
| 2008/0167573 A1* | 7/2008 | Stivoric ............ G01K 1/022 |
| | | 374/E1.004 |
| 2008/0297617 A1* | 12/2008 | Jeong ............ H04N 5/23219 |
| | | 348/222.1 |
| 2009/0284380 A1 | 11/2009 | Chen |
| 2010/0205667 A1 | 8/2010 | Anderson et al. |
| 2010/0284592 A1 | 11/2010 | Arnon et al. |
| 2011/0050432 A1 | 3/2011 | MacSween |
| 2014/0333412 A1 | 11/2014 | Lewis et al. |

FOREIGN PATENT DOCUMENTS

| | | | |
|---|---|---|---|
| DE | 102007056915 A1 | 5/2009 | |
| EP | 1257118 A1 | 11/2002 | |
| WO | WO-2010048505 A1 * | 4/2010 | ............ G01J 5/061 |

OTHER PUBLICATIONS

Pompei, Non-Invasive Temporal Artery Thermometry: Physics, Physiology, and Clinical Accuracy.

* cited by examiner

| TIMESTAMP | SCANNER ID | SENSOR ID | TEMPERATURE | IMAGE DATA |
|---|---|---|---|---|
| 10/30/2012 7:50:45 AM | [3698] | 9096 9097 9621 | 97.20°F 91.30°F 83.30°F |  |
| 10/30/2012 8:39:17 AM | [3698] | 9278 9288 9621 | 86.30°F 86.30°F 81.80°F |  |
| 10/30/2012 9:25:55 AM | [3698] | 9096 9097 9621 | 97.90°F 94.60°F 81.60°F |  |
| 10/30/2012 9:45:16 AM | [3698] | 9096 9097 9621 | 97.60°F 92.40°F 81.50°F |  |

SYSTEMS FOR REAL TIME FEBRILITY DETECTION AND NOTIFICATION

BACKGROUND

Field of the Invention

The technology relates to systems and processes for use in infectious disease screening, and more particularly, to systems and processes for determining a febrile condition in persons in a monitored zone.

Description of the Related Art

It has been become increasingly necessary to detect and identify people that may be infected with a contagious illness, whether bacterial or viral. People are very mobile, traveling from city to city and country to country often within the span of a single day, and that factor makes it even more important to identify infected persons, to prevent or at least minimize the potential for the spread of disease. Rapid detection and isolation of a "super spreader" early in an outbreak can be the difference between a micro-outbreak that fizzles out and a facility-wide or regional epidemic. In recent years there has been mounting concern about such international infectious diseases as SARS in recent years, and concerns about infections transmitted in hospitals, among sensitive locations. There is a consensus that elimination of transmission of a contagion through detection and isolation of infected individuals may be an effective tool in avoiding the spread of the contagion. Further suggested is that although we all carry contagions even if not symptomatic, an infected and symptomatic person is many orders of magnitude more capable of infecting others with direct contact. In addition, a febrile person is capable of leaving infection in the air, on the ground, on surfaces and throughout the environment of the facility while he/she is in the facility, whether working, volunteering or visiting.

In certain facilities, such as hospitals, it has become an accepted practice to use a form of "health credentialing" to permit access to the facility. "Health credentialing" is a safeguard that is intended to assure the facility granting access to an individual that the particular individual being allowed access is free of any communicable disease or infection. For example, when a business has employees that frequently access a facility, like a hospital for example, where contagion is of concern, it may retain a credentialing service organization to vet its employees and regular visitors. This credentialing service organization identifies and screens all employees and regular visitors of the business, typically at a periodic interval, such as annually or bi-annually for infection and also checks that they are up to date on any inoculations. Once the screened persons are credentialed as being free of infectious disease and inoculated, meeting the requirements of the health care institution facility, the facility remits access badges to the employees and regular visitors thereby permitting access to the facility. The facility allows access until the health credential expires. Typically, such health credentials expire in one year, after which the persons must undergo re-screening and or inoculation, as required. The employee or regular visitor may not be tested again for the other 364 days of the year for their capability to spread an infection. This system, therefore, ignores the potential of a credentialed person becoming infectious between periodic screenings and leaves open multiple daily possibilities for infection to spread into the facility, despite credentialing.

SUMMARY

Systems and processes are presented for real time health credentialing of individuals seeking entry to a facility requiring health credentialing for access. A system and process for real time detection of a febrile condition comprises providing a heat sensor operable to receive thermal radiation from a person. Optionally, the system provides a controller operable to selectively orient the thermal sensor incident to the facial region of a person within a zone of detection. Further, the system optionally processes the sensor temperature to conditionally determine a febrile condition.

BRIEF DESCRIPTION OF THE DRAWINGS

The following drawings are not to scale and are provided for ease of explanation. The figures depict exemplary embodiments, and do not limit the scope of the invention, as defined in the claims, here below:

DETAILED DESCRIPTION

Figure 1:
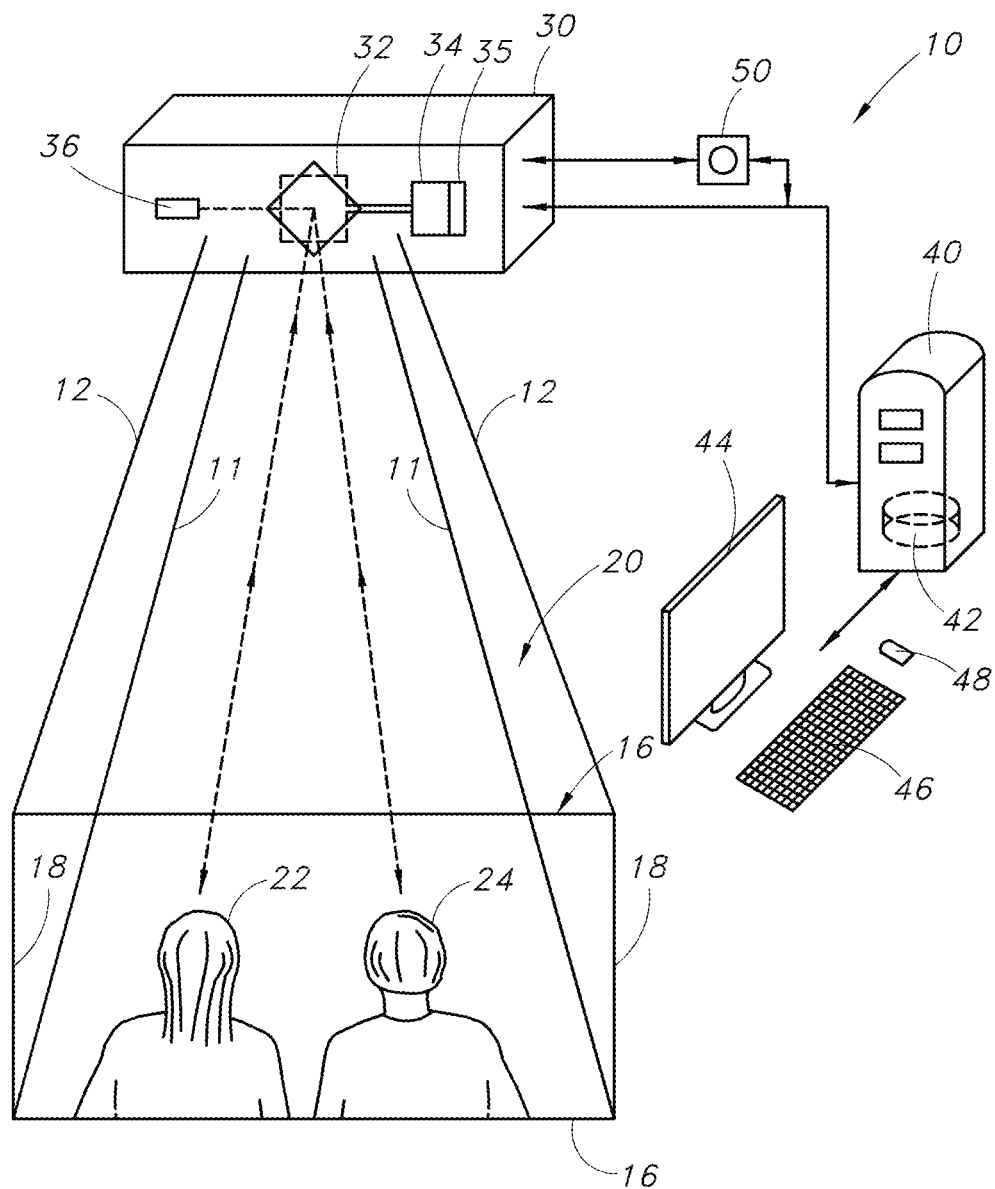
FIG. 1 is a schematic view of an exemplary real time health credentialing system.

The following detailed description provides a description of exemplary embodiments of the technology claimed here below to facilitate an understanding of the technology, but does not limit the scope of the technology claimed.

It is apparent that health credentialing systems that rely on only a periodic test have a major flaw: the tested individual may have acquired a contagious infection after the testing for health credentialing has taken place and before the next scheduled test. This represents a clear risk to the facility that is attempting to eliminate or reduce the risk of inborn infectious disease carried by those who enter its facility. However, it may not be cost-effective nor practical to test each individual requiring access to the facility for a wide range of potential infectious diseases using traditional means such as manual inspection, body fluid analysis, and the like. Accordingly the exemplary embodiments presented herein, the temperature of an individual requiring access is used as an alternate testing for an individual having a wide range of infectious diseases. It has been found that a febrile condition in a person is a strong indicator of whether that person has an infectious disease and may be in a condition to spread harmful doses of contagion.

The temperature of an individual may be measured by a variety of instruments. Contact sensors may be used, but these require physical contact with a subject and would be suitable for single person point testing in an unconstrained time environment but not for scanning consistent ingress of persons seeking access to a facility. Among the commonly available contact sensor instrument alternatives is a heat sensor, such as an infra-red heat sensor. Since energy related directly to heat is in the band commonly referred to as "far infrared," or 4-14 µm in wavelength (4,000 to 14,000 nm), this is the preferred range for infra-red measuring of skin temperatures.

A person's core body temperature (TC) is a key factor in making a determination about whether an individual is exhibiting a febrile condition. However, TC varies from one individual to another, and is therefore not the same for all persons, although 98.6° F. is regarded as "normal," i.e. not febrile. A more accurate determination of whether a particular person has a febrile condition is to accumulate a database of that specific person's temperature over a period of time and to obtain a baseline TC from that data for that individual. Any upward excursion from that base TC could then be assessed statistically to state with a degree of confidence whether that particular person has a febrile condition. However reading TC is often invasive, and time consuming, expensive or inconvenient. Accordingly, skin temperatures (TS) are measured. Often, these skin temperatures are less reliable. But, when skin temperature is measured by infrared scanning, across the face and neck, the peak temperature, which is the one selected by exemplary systems, is the temperature found in the most vascular part of the face. This temperature might be, for example, on the skin overlying the temporal artery or carotid arteries. Those vessels are closest to the surface and carry blood recently pumped from the heart and only inches away from it. Accordingly, in an exemplary embodiment, skin temperature may be used as a basis for determining a febrile condition with a high level of confidence.

In an alternative embodiment, an algorithm may be used to estimate the person's core temperature, with knowledge of both his or her skin temperature and the ambient temperature (TA). Exemplary embodiments of a real time health credentialing system may include a local or remote with a database in its memory. An exemplary database may include a separate file for each person seeking access or that has to be credentialed. The file contains at least information about the person's identity, including, but not limited to, for example any or all of: name, place of employment, address, and facial recognition data. In addition the person's file may include temperature data, such as for example: previous temperature readings, and time at which these temperatures were taken, along with ambient temperature at the time of the temperature reading. The information from a scan, such as skin temperature and ambient temperature are processed to determine whether the particular person, identified by his database file, has a fever. Thus, at time of scanning the person, a calculation using a formula of the following type may be carried out at the server: $TC=(1+h/pc)(TS-TA)+TA$. The term $h/pc$ is a coefficient used to approximate the heat loss at skin temperature based on three parameters: h, which is empirically derived; p the perfusion rate; and c the specific heat of blood. These parameters vary based on the tissue being measured and is clearly lower for tissue that is closer to core temperature such as oral, ear drum/canal and then higher for extremities. In general, the ratio $h/pc$ may vary from about 0.05 to about 0.50. Commonly, $h/pc$ is estimated at about 0.19.

The foregoing calculation provides a more accurate core temperature as a basis for determination of a febrile condition with a high level of confidence and low number of "false positives." This is a significant advantage since each false positive may result in improper determination of a febrile condition, which in turn may lead to improper denial of access to the subject facility.

In general, when a person wants to enter a facility, they walk through an entry area or focal point, such as a passage or hallway after or before entry through a doorway. Thus, they are in a controlled volume of space that is amenable to being scanned, for example by optical scanning, scanning with a video camera, and scanning with an infra-red sensor that scans the controlled volume of space. Depending on the volume, number of people, and other factors, further scanning may be desirable to scan the entire volume of space wherein the persons are present. Rather, only the subset of the entire volume of space containing the facial features of the subject persons are likely to be scanned for temperature processing and analysis. This subset will permit both facial recognition and a reading of facial skin temperatures as efficiently as possible with the least volume to be scanned for facial skin temperature measurement and processing. Indeed, facial recognition technology using a camera might be useful to both identify and also target the person's face and controllably guide a heat sensor to take readings of his or her facial temperatures. This might minimize the extent of motion for scanning necessary for the heat sensor.

The following examples of the inventive technologies may be used in a variety of facilities and setting, for example, hospitals, nursing homes, food processing plants, pharmaceutical manufacturing facilities, and other work places where it is desirable or necessary to minimize risks of spreading any kind of infectious illness. One way of addressing that issue is to identify febrile persons and to take steps to either exclude those persons from the facility or take other suitable precautions. Thus, examples of a "real time health credentialing" technology of identification, temperature detection, and febrile condition determination are presented.

The invention incorporates a heat sensor 30 of various configurations. In a first configuration, the heat sensor 30 is fixably mounted where it or the cooperatively joined housing can be manipulated to control the heat sensor's 30 input. In a second configuration, the heat sensor 30 is pivotably mounted such that the heat sensor's 30 orientation may be manipulated to control the heat sensor's 30 input. In a third configuration, the heat sensor 30 is fixably mounted and in thermal communication with a fixably mounted reflector 32 which directs thermal radiation upon the heat sensor 30. In a fourth configuration, the heat sensor 30 is fixably mounted and in thermal communication with a pivotably mounted reflector 32 which directs thermal radiation upon the heat sensor 30. It is to be understood that other heat sensor 30 configurations are within the spirit of this invention.

The system optionally adjusts the temperature received from the heat sensor 30 based on the distance of the subject. The system can employ a distance sensor (not pictured), image data from a camera 50, or other means in the art to determine the distance of the subject.

The exemplary embodiment of FIG. 1 depicts a system for real time health credentialing that includes a scanning heat sensor 30. The scanning heat sensor 30 includes a reflector 32 that is coupled to a servo-motor 34 such that the reflector 32 moves in a controlled manner as the motor is driven. The reflector 32 is thermally coupled to the sensor adding accuracy to the thermal measurement. The coupling between the motor 34 and the reflector 32 may include a camming device that will cause the reflector 32 to move in a preset pattern. When in motion, the reflector can capture images within a controlled volume, designated as its detection zone 20. In the illustrated example, the detection zone 20 is rectangular in cross section and located such as to encompass the facial regions of persons 22 within the detection zone 20. The detection zone boundaries are discussed more fully later with reference to FIG. 2.

In FIG. 1, a heat sensor 36, such as an infra-red detector, is aligned to receive a signal 38 along the reflector 32 so that it is reflected inward from the detection zone 20. As the reflector moves, the infra-red signal 38 will, by design, scan the facial regions of persons 22, 24 and detect their respective temperatures.

A camera 50, equipped to zero in on facial features, focuses on the facial features of the persons 22, 24 and sends facial recognition image data to a server 40 that has a database 40 including facial recognition data for persons that might be allowed access, if appropriately credentialed. Server 40 may be located on site or remotely. In an alternative embodiment, the reflector 32 may move in response to a signal from a camera 50 (rather than in a pattern set by a camming system) to a controller 35 of motor 34 that specifically directs the orientation of the reflector 32 to a face of a person for heat scanning, and to capture an image of each person in a crowd for such heat scanning. That is to say that the heat sensor 30 or reflector 32 is cooperatively oriented to receive thermal radiation form the position of the face determined by optical camera 50 and system processing. In addition to optical facilitation of recognition of faces within the detection zone 20, the system may employ facial region recognition using heat differentiation. Where the heat sensor 30 receives a temperature within the a range for the possible subjects, that area is selected as a possible facial region.

Within the facial region, the heat sensor 30 may be oriented to receive thermal radiation from selected areas of the face. The preferred areas are the forehead, nose bridge, inner canthi, and temples. Where a facial region is located, the heat sensor 30 can scan that local region, effectively enabling the system to produce a thermogram for that facial region. Using empirical facial thermal signatures and patterns, the system can orient the heat sensor 30 to receive thermal radiation from preferred areas of the facial region. Additionally, the system may employ image data from the camera 50 to provide fine orientation of the heat sensor 30.

Figure 7:
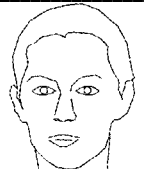
FIG. 7 is a representative partial schema of historical temperature.
Figure 7:
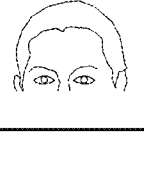
Figure 7:
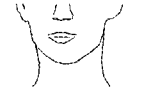
Figure 7:
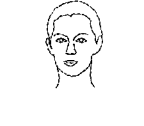

Temperature information about each of persons 22, 24 (and as many as are present and scanned) are transmitted to a database 42 of the server 40. FIG. 7 illustrates a representative partial database schema of historical information. Illustrated data includes a timestamp, a scanner identifier, a sensor identifier, ambient temperature, skin temperature, core temperature, and image data.

Software including an algorithm on the server 40 determines whether persons 22, 24, each identified by facial recognition technology, have a febrile condition, as explained above. The server 40 may have visual output on monitor 44 at a workstation that may also permit data input, for example via keyboard 46 and mouse 48. In an optional embodiment, the system provides an alert when a febrile condition is detected. The alert may be audible, visual, or both and may also be transmitted to appropriate parties wirelessly or by other means.

Figure 2:
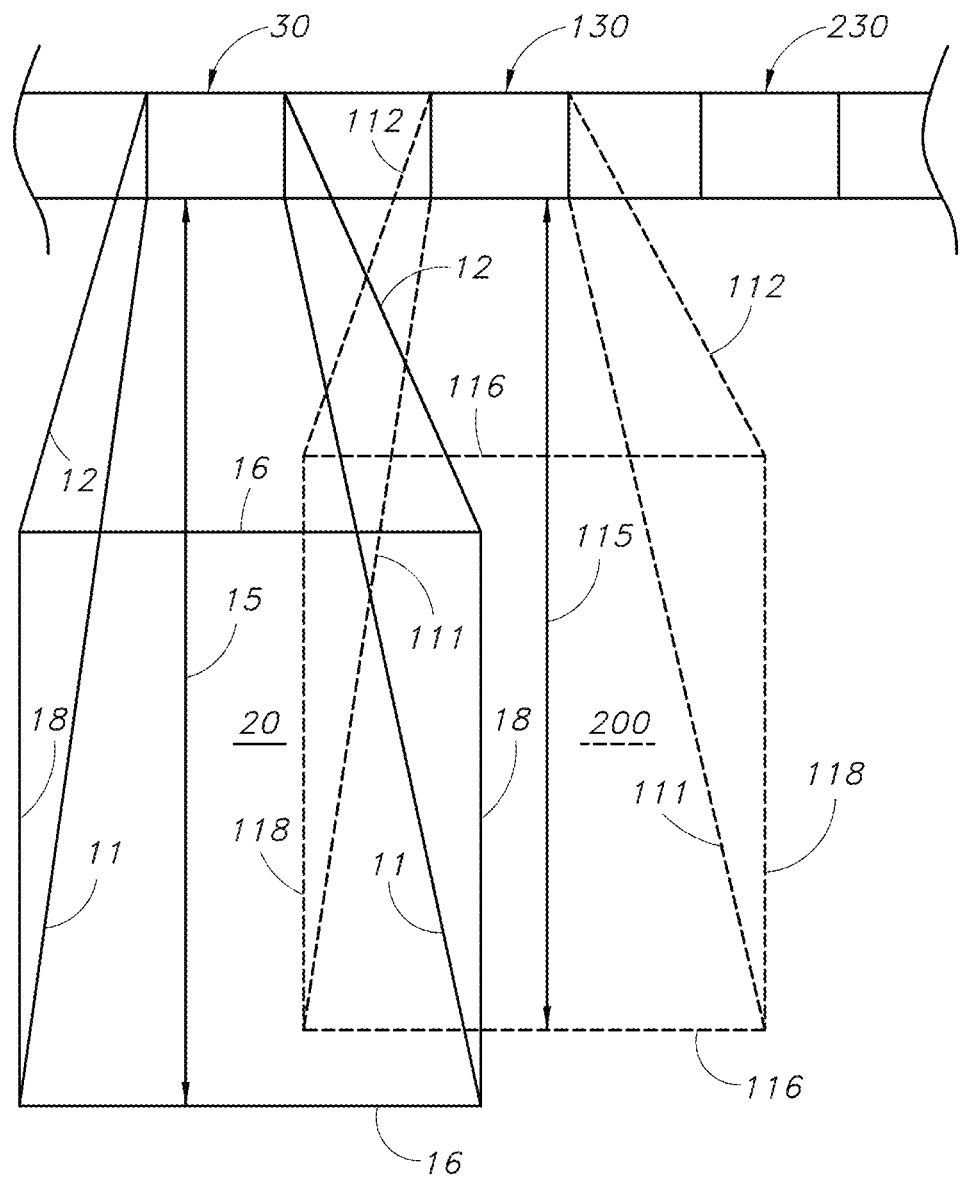
FIG. 2 depicts a schematic view of a series of scanners placed adjacent each for real time health care credentialing.

The exemplary embodiment of FIG. 2 illustrates a series of scanning heat sensors 30, 130 and 230 mounted at spaced intervals to determine febrile condition in real time for persons seeking access to a facility. In the illustrated example, the detection zones may overlap, although that overlap is not necessary. The detection zone 20 of scanning heat sensor 30, at a distance 15 from the seaming heat sensor, is defined by a volume 20. The volume 20 has a rectangular vertical face having a perimeter of a pair of vertical opposed sides 18 and horizontal opposed sides 16; and the longitudinal sides of the volume 20 are defined by longitudinally lower extending opposed sides 11, 11 and upper extending opposed sides 12, 12. Likewise, scanning heat sensor 130 has a detection zone 120 that overlaps with detection zone 20, in the illustrated example. The volume 120 has a rectangular vertical face, at a distance 115 from the scanning heat sensor 130, having a perimeter of a pair of vertical opposed sides 118 and horizontal opposed sides 116; and the longitudinal sides of the volume 120 are defined by longitudinally lower extending opposed sides 111, 111 and upper extending opposed sides 112, 112. The detection zone for scanning heat sensor 230 is not drawn out for the sake of brevity and may be regarded as similar to those of scanning heat sensors 30 and 130. Detection zones not of the shape presented in these examples are within the spirit of this invention, as detection zone shapes may vary widely.

Figure 3A:
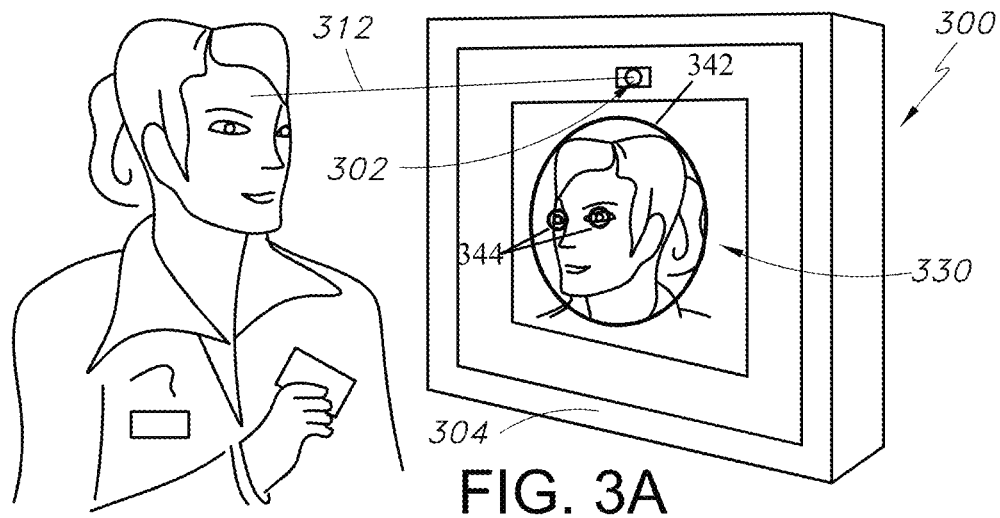
FIG. 3A is a schematic illustration of an exemplary embodiment of a device for health care credentialing that utilizes facial recognition data.

The identity system may include any of: an alphanumeric identifier, a bar code scanner, a RF detector for a smart card, a biometric type of identifying device such as, for example, a hand/fingerprint scanner, a card reader, a QR code, or an optical scanner that may be used to uniquely identify an individual. An exemplary embodiment of a temperature and facial recognition device that may be used to identify an individual and also detect a febrile condition in the individual is shown in FIGS. 3A and B, and a system utilizing a plurality of such devices is shown in FIG. 3C. Referring to FIGS. 3A and B, an individual approaches the temperature and facial recognition interface 300 and stands in front of it so that a camera 322 may detect and capture an image of his face. Standing in this position, an infrared sensor 310 may scan through aperture 302 in housing 304 to find temperature one or more temperature readings from his face, in the case of a device equipped with a scanning mirror 314, such as described here below with reference to FIGS. 4A and B. Alternatively, if the infrared sensor 310 has a static (or non-scanning) mirror 314, then he might be instructed as to how to position his face relative to the interface 300 to ensure the best temperature reading. Optionally, the interface 300 may be equipped with a visible light beam emitter 315 that is aligned with the center of the scanning volume of the infrared sensor 310 in order to better guide the person and obtain the best temperature reading. For example, using such a light emitter 315, the individual may see his face in a display monitor 330 indicating the position of the visible light (e.g. red or other colored) "dot" of the incident light beam, and may be instructed to move his face such that the light beam (and hence the sensor 312) is incident upon a desired region of his face, such as the forehead, nose bridge, inner canthi, or temples. The light emitter 315 may be, for example, an LED emitting a concentrated beam of visible light. An alternate guide includes a circular overlay 342 on the display monitor 330 to indicate facial placement. The alternate guide may includes smaller inlaid circular overlays 344 as a more refined indicator for eye alignment.

Thus, this example of an embodiment of the device permits (1) identification by facial recognition, as well as (2) determination of febrile condition. Of course, in alternative embodiments other means of identification may also be used, such as a RFID reader, a bar scanner, etc., as explained above.

Figure 3B:
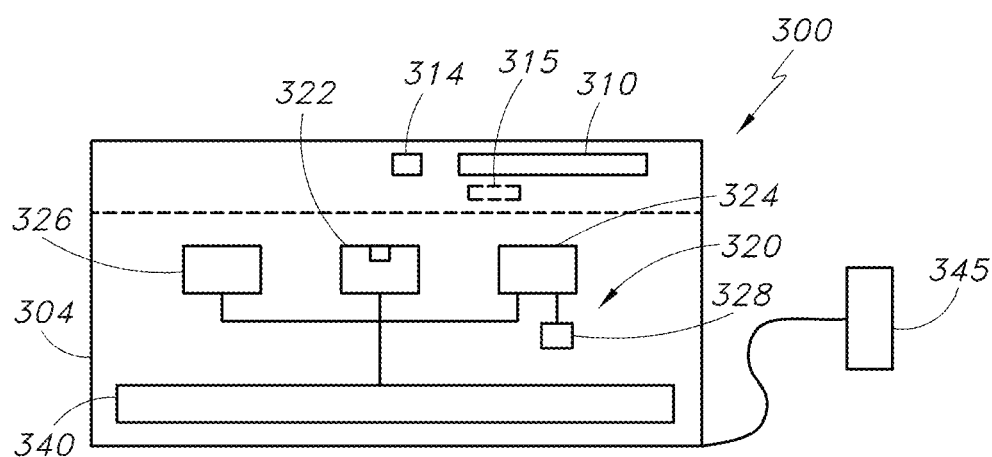
FIG. 3B is a schematic block diagram of the device of FIG. 3A.
Figure 3C:
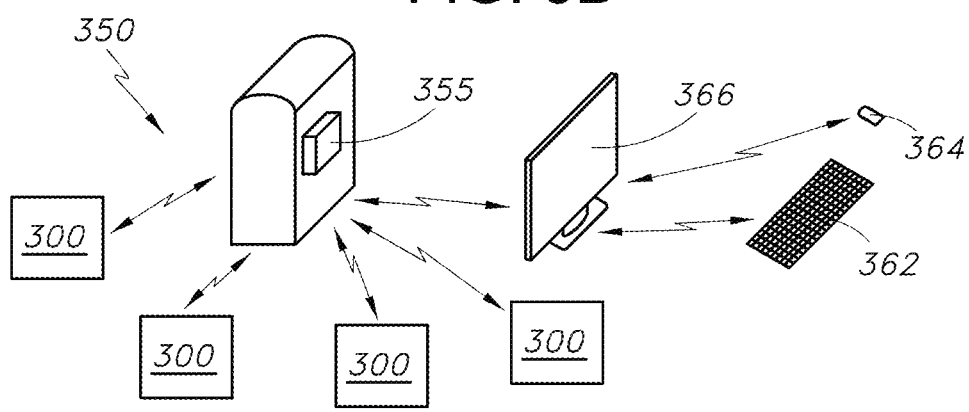
FIG. 3C is a schematic illustration of a system that includes a plurality of devices of FIG. 3A.

The exemplary temperature and facial recognition device 300 shown in FIG. 3B includes an outer housing 304. The camera 322 may advantageously be a front mounted camera of a tablet computer 320, or may be any other camera. However, in the particular example shown, the camera 322 is a component of such a tablet computer 320 and the infrared sensor 310 may be within the same housing 304 or in an adjacent housing. Regardless of housing location, the infrared sensor 310 is paired to, and in electronic communication with, the tablet computer 320. The tablet computer 320 further comprises at least a CPU 324, a memory module 326 configured with a database of facial recognition data for a population, a communications module 328, and a display monitor 330. The tablet computer may also have a battery 340 and/or may be connected to a source of electricity, such as a wall outlet 345.

In use, the exemplary temperature and facial recognition device 300 carries out several steps. The camera 322 scans and captures an image of the facial features of an individual in front of the device 300. The CPU 324 is configured to analyze the captured image using facial recognition software configured. The memory module 326 includes a database of facial recognition data for each individual in a population that is to be identified and whose temperature is to be determined to ascertain a febrile condition. Thus, the analyzed facial data captured by the camera 322 and analyzed by the CPU 324 is compared to the facial recognition data stored in memory 326. If there is a match, the person is identified, and his/her name may optionally be displayed on monitor 330, as a check. Further, the infrared temperature sensor 310 senses the temperature of the individual and the sensed temperature may be used to detect a febrile condition. Temperature information about the individual may be compared with previous temperature data for that individual stored in the database. Software including an algorithm, as detailed above, may then be used to determine whether the individual has a febrile condition, as also explained above.

FIG. 3C illustrates an example of a system that includes a plurality of temperature and facial recognition devices 300, each in communication with a central computer or a cloud computing network 350 where the facial recognition data of the population is maintained and stored in memory 355. The central computer or cloud computing network 350 is accessible to control personnel through a user interface including a keyboard 362, mouse 364 and display monitor 366.

Figure 4A:
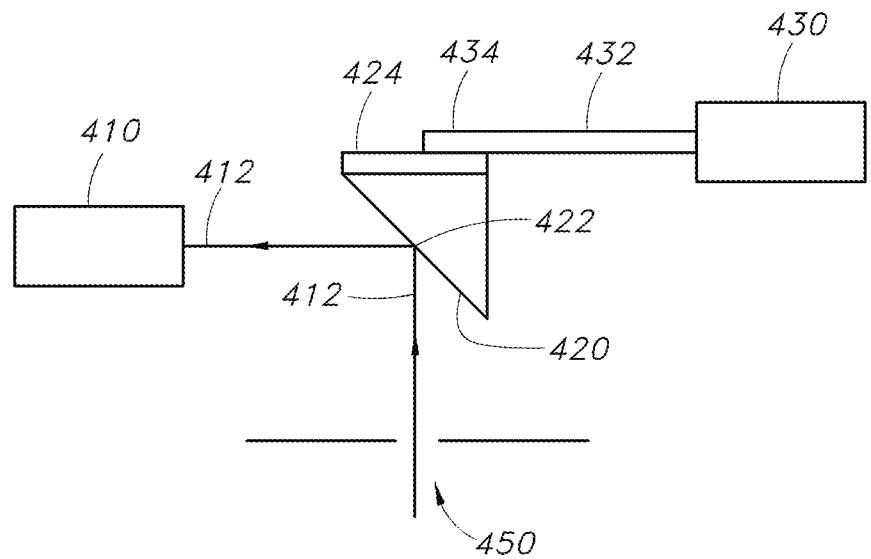
FIG. 4A is a schematic depiction of a portion of an embodiment of a scanning device used to detect a febrile condition.
Figure 4B:
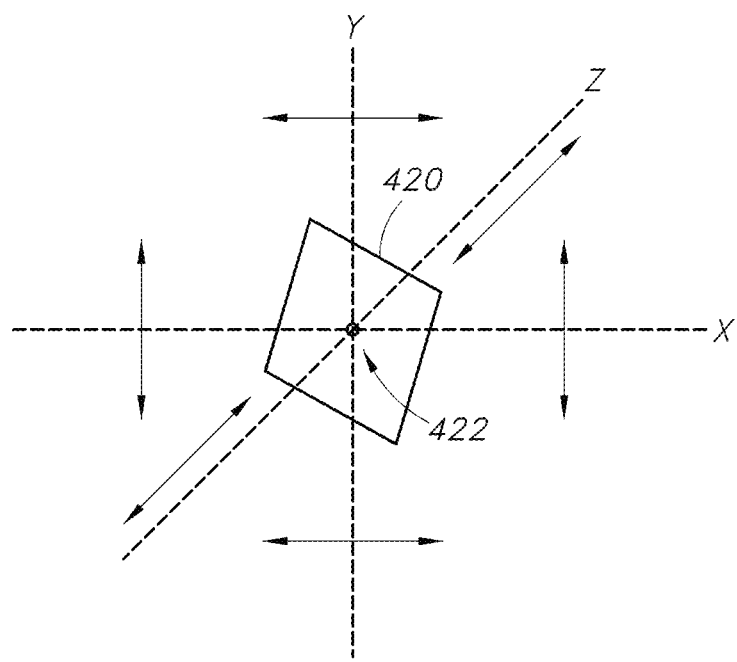
FIG. 4B is a schematic depicting the three dimensional motion of a mirror used in the exemplary embodiment of FIG. 4A.

An exemplary embodiment of a system for selectively orienting a reflector 420 for use in a scanning heat sensor is depicted in FIGS. 4A and 4B. In FIG. 4A, the exemplary components for a scanning infrared heat detection are shown: a stationary infrared sensor 410 scans incident images projected from a mirror 420, which is angled to deflect the infrared radiation 412 incoming through an aperture 450, to the sensor 410. In this embodiment, the infrared sensor 410 must scan a volume of space to find the person and to detect a febrile condition, preferably by heat detection on the facial area, and especially on or around the forehead, nose bridge, inner canthi, or temples. To achieve such scanning, the mirror 420 tilts (i.e. moves in three dimensions) about its center point 422 through three dimensions to thereby scan the space, as appropriate and necessary, to reflect infrared radiation from the scanned space to the infrared sensor 410. As shown schematically in FIG. 4B, the mirror 420 has a center point 422, and while that center point is relatively static, the mirror 420 is configured for selective, granular control in the x, y and z axes, as shown, maximizing infrared radiation 412 receipt from vantage points within the zone of detection 20 120 220. Thus, for example, when the upper end of the mirror 420 moves to the left, the lower end moves to the right, and vice versa. Similarly, backward motion in the z-direction of one side of the mirror 420 results in forward motion of the opposite side of the mirror 420. Motion in the y-direction takes place similarly. Thus, the motion in three dimensions ("tilting") causes the region from which infrared radiation originates to be incident on the mirror 420 to change i.e. to selectively and controllably receive infrared radiation emitted within the zone of detection 20 120 220.

In the exemplary embodiment shown in FIG. 4A, the tilting of the mirror 420 is effected by mechanical camming action, although other schemes may also be used. A surface 424 at the rear of the angled mirror 420 is shaped to cooperate with a surface 434 on the end of a spindle 432 of a motor 430. Thus, as the motor rotates the spindle 432, the spindle end-surface 434 rotates and urges against the mirror rear surface 424 causing the rear surface 424 (and hence the mirror itself 420) to move in response to it. By selectively shaping surfaces 424 and 434, the motion of the mirror 420 and hence the scanning pattern of the sensor 410 (represented schematically by incoming infrared radiation 412 through aperture 450) be controlled.

Figure 5A:
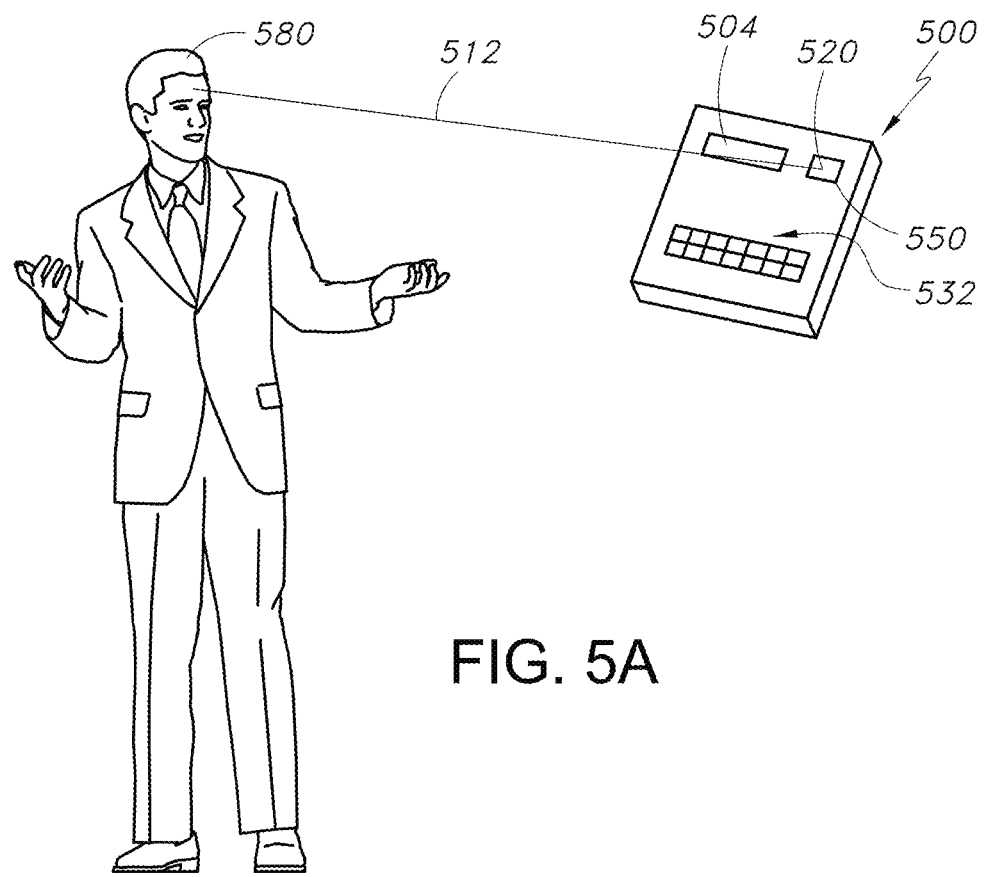
FIG. 5A is a schematic depiction of an exemplary embodiment of a hand-held device used to detect a febrile condition.
Figure 5B:
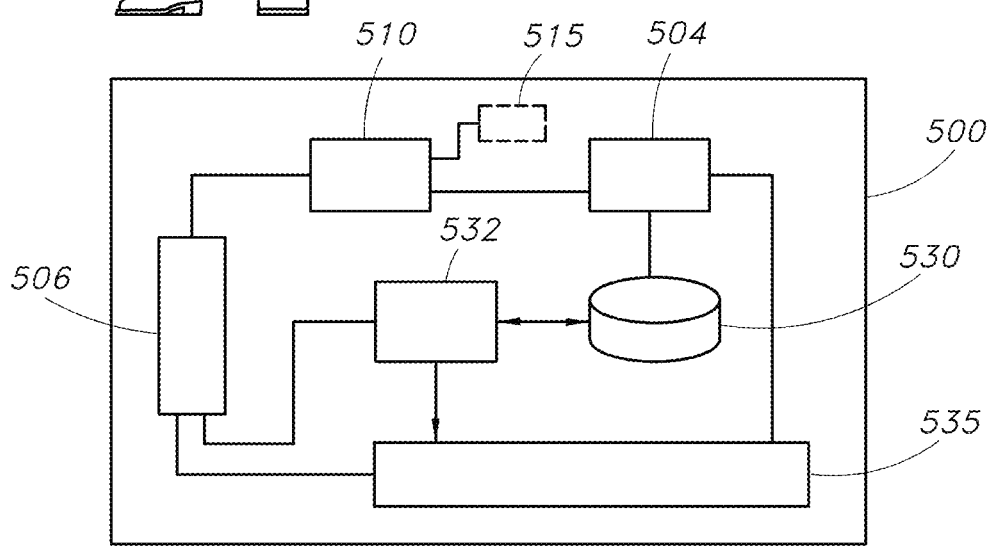
FIG. 5B is a schematic block diagram of internal components of the embodiment of FIG. 5A.

In a further exemplary embodiment, there is provided a hand-held, portable battery-powered sensor for detecting a febrile condition. An exemplary embodiment is depicted in FIGS. 5A and B. In this depicted example, the hand-held sensor 500 has an infrared sensor 510 that receives incoming infrared radiation entering the hand-held device 500 through an aperture 550 of the sensor 500, and reflected off mirror 520. The person 580 holding the sensor 500 manipulates: the sensor 500 while observing his/her reflection in a highly-polished, mirror-surfaced frontal surface 502 of the sensor 500. The surface 502 should not absorb (or only minimally absorb) infrared energy in the wave length emitted by the emitter 510, and may be steel, for example. Thus, the person 580 can manipulate the sensor until the infrared scanner 510 is in position to scan his/her forehead, nose bridge, inner canthi, or temples to read his/her temperature to detect a febrile condition. The temperature may then be displayed on an output display 504 powered by battery 506. In an option exemplary embodiment, the hand-held device 500 may be equipped with a visible light beam emitter 515 that emits a visible light beam 512 that is aligned with the infrared sensor 510. This will allow the user to see a visible light spot on his/her face and to manipulate the device 500 until the spot is incident upon his/her temple, for example, to obtain the best temperature reading. Reading at the same location on the face as a routine practice may also improve the reliability of the device 500 in predicting a febrile condition.

In other exemplary embodiments, the temperature may be stored in a memory 530, along with the date and time, for access later. The memory 530 may store data for one or more individuals, such as a family, for example. A CPU 532 may be programmed to utilize stored data for an individual (or more than one individual) to better determine whether that particular person has a febrile condition. Normal body temperature, and normal body temperature range, can vary significantly from one person to another. Moreover, the sensor 500 may have a user interface 535 to facilitate user extraction of temperature information and to input information such as date, and time or to identify a particular user, where there are more than one user.

It has been found that environmental temperature fluctuations may cause temperature fluctuations of measuring devices resulting in slight but significant variations in temperatures sensed. These variations may affect the determination of whether or not a person is likely to have a febrile condition. Accordingly, it is recommended that the devices be shielded to avoid or at least minimize temperature fluctuations of the device its self. This can be achieved by suitable application of heat insulating material around the infrared sensor, for example, such as Mylar co film, or another light weight and relatively thin insulating material.

An exemplary embodiment of a device for detecting a febrile condition may use an infrared sensor of a type that does not require a mirror to scan the volume of space within which at least the face of the subject to be scanned may be found. This allows the device to dispense with the mirror as well as the motor that drives the mirror, as exemplified in FIGS. 4A and B. This results in a lighter and potentially more compact device. A non-limiting example of an infrared sensor of this kind, is for instance, the MLX90614 sensor of Melexis Microelectronic Systems of Ieper Belgium.

Figure 6A:
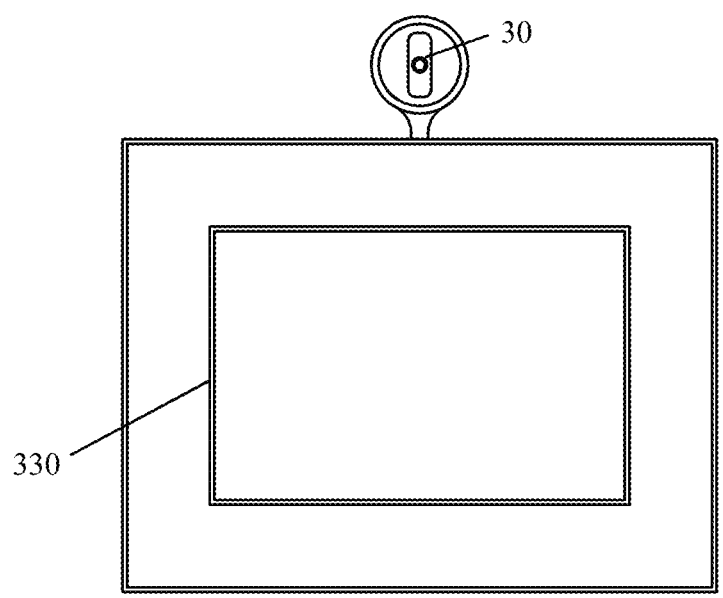
FIG. 6A is a front view of an example of a thermal sensor mounted to a controller.
Figure 6B:
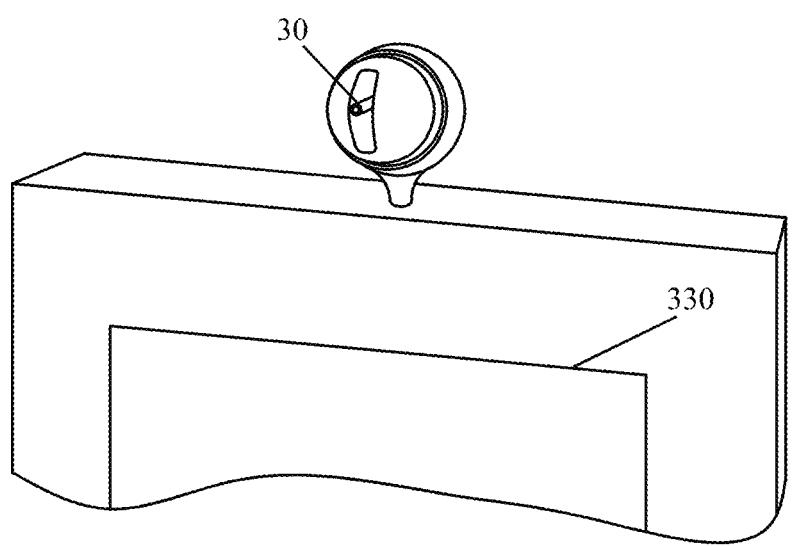
FIG. 6B is a side perspective view of the device of FIG. 6A.

FIGS. 6A and 6B depict an infrared sensor attached to 12C bus to an FTDMI USB 12C bus converter for direct computer control of the heat sensor 30. As can be seen, when mounted in place, the sensor is generally perpendicular to the planar surface of the mount and points out of an aperture to scan the volume of space in front of the device. In the example of the figures, the sensor is shown mounted on a rocker arm that has a cam follower. But, it may in the alternative, the sensor may also be rocked by voice coil/magnetic control under any of the below two adjacent arms.

Figure 8:
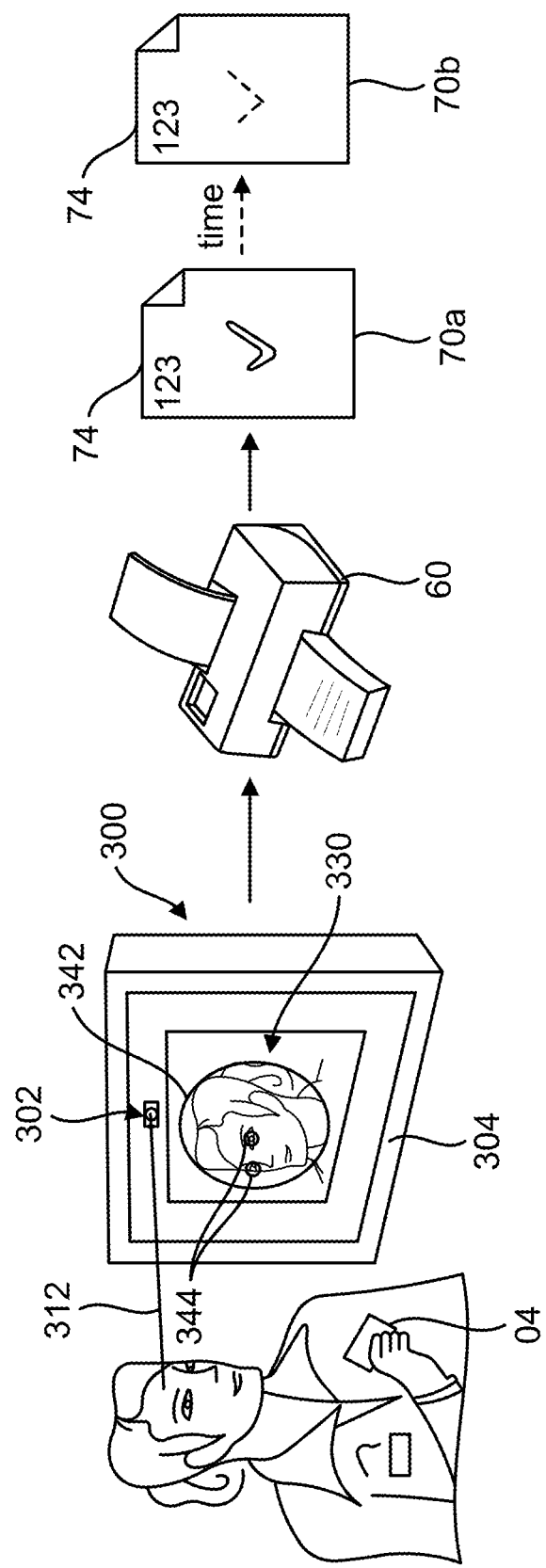
FIG. 8 is a schematic view of an alternative real time health credentialing system.

FIG. 8 depicts another embodiment of the invention further comprising a printer 60 in communication with the temperature system. In exemplary configuration, the printer 60 receives a permission message 72 to restrict ingress, deny ingress, or allow ingress based on the temperature condition of the person and identity information. The printer 60 generates a print 70 based the received information. In one configuration, the printer 60 generates the print 70 using a time sensitive ink or ink display system, that is to say an ink which changes appearance over time. It may disappear or change color in response to exposure to light, air, heat, pressure, humidity, or other conditions. A representative ink and ink display system is disclosed in U.S. Pat. No. 5,633,835 to Haas, which is hereby incorporated by reference, U.S. Pat. No. 5,989,700 to Krivopal which is hereby incorporated by reference, U.S. Pat. No. 8,622,436 to Mehta et al. which is hereby incorporated by reference, and U.S. Pat. App. No. 20120014740 to Kamitani et. al. which is hereby incorporated by reference.

Exemplary information for receipt from the temperature system includes identity information and the febrility information of the person. Representative print 70 surfaces include paper or sticker. In one configuration, the permission message 72 is textual. In another configuration, a visual indicator (depicted as a check mark) is used to represent the permission message 72.

At facilities such as airports, hospitals, nursing homes, food processing plants, or other places, the print 70 is used to effect the ingress/egress permission message. An exemplary print 70 includes the identity information 74, the permission message 72, and a time stamp of the generation of the print. The information of the print 70 is optionally encoded, encrypted, or represented in alternate formats such as a QR code.

The foregoing description provides examples of embodiments of the facial temperature monitors and does not limit the inventions, which are defined only by the appended Claims. The scope of the inventions includes any modifications and supplementations that a person of ordinary skill in the art may perceive upon reading this disclosure. Further, the scope of the claimed inventions includes any equivalents that a well-informed court may provide under the doctrine of equivalents.

The invention claimed is:

1. A system for real time detection of a febrile condition, the system comprising:
    an interface comprising a housing and a display presenting a zone of detection in front of said display;
    a scanning heat sensor comprised of an infrared sensor, a distance sensor, and a mirror configured to deflect infrared radiation incoming through an aperture in said housing to said infrared sensor;
    wherein said mirror is further configured to move in three dimensions by mechanical camming action so that said mirror selectively and controllably receives infrared radiation emitted from a selected area of a facial region of a person within said zone of detection;
    wherein said selected area of said facial region of said person within said zone of detection comprises said person's forehead, nose bridge, inner canthi or temples;
    wherein selection of said selected area of a facial region of said person is based on heat differentiation;
    said interface further comprising a guide system operable to facilitate position of said facial region of said person relative to said scanning heat sensor;
    said system transmitting a permission message to restrict ingress, deny ingress, or allow ingress based on a temperature condition of said person;
    said temperature condition comprising a determination of whether said person has a fever based upon processing of information comprised of ambient temperature, said person's core body temperature, said person's skin temperature, heat loss at skin temperature, and said person's distance from said scanning heat sensor.

2. The system of claim 1, wherein said guide system comprises a camera oriented toward said zone of detection in communication with said display, wherein an output of said camera is transmitted to said display showing the face of said person; and
    a circular overlay is shown on said display operable to signal optimal facial position.

3. The system of claim 2 wherein said guide system further comprises an additional smaller, circular overlay inlaid within said first overlay, operable to signal optimal eye position.

4. The system of claim 1, wherein said scanning heat sensor is configured to receive thermal radiation from said facial region of said person from at least one of the following: temple, forehead, nose bridge, canthus, neck.

5. The system of claim 1, wherein said scanning heat sensor is configured to receive thermal radiation from said facial region of said person from the inner canthus.

6. The system of claim 1 further comprising an identity system.

7. The system of claim 6, wherein said identity system comprises an optical camera in communication with a facial recognition database, said optical camera pivotably mounted proximate said zone of detection and providing identity information for said person.

8. The system of claim 6, wherein said identity system comprises an RFID reader in communication with a person database, said RFID reader providing identity information for said person.

9. The system of claim 6, wherein said identity system comprises a bar code reader in communication with a person database, said bar code reader providing identity information for said person.

10. The system of claim 1, further comprising a processor and memory configured to receive input from said scanning heat sensor and associate said input with a person.

11. The system of claim 1, further comprising a printer configured to receive said permission message and print a representation of said permission message.

12. The system of claim 11, wherein said printer includes a time sensitive ink or ink display system.

13. The system of claim 11, wherein said representation of said permission message includes at least one of a time stamp or an expiration time.

14. The system of claim 1, wherein the scanning heat sensor comprises an infrared sensor that is surrounded by a heat insulating material.

* * * * *